(12) United States Patent
Ellis

(10) Patent No.: US 10,786,407 B2
(45) Date of Patent: Sep. 29, 2020

(54) CHEMO MOBILE CART SYSTEM

(71) Applicant: Cardon Ellis, Newhall, CA (US)

(72) Inventor: Cardon Ellis, Newhall, CA (US)

( * ) Notice: Subject to any disclaimer, the term of this patent is extended or adjusted under 35 U.S.C. 154(b) by 225 days.

(21) Appl. No.: 16/007,110

(22) Filed: Jun. 13, 2018

(65) Prior Publication Data
US 2019/0380894 A1 Dec. 19, 2019

(51) Int. Cl.
| | |
|---|---|
| A61G 5/10 | (2006.01) |
| B60D 1/14 | (2006.01) |
| B60D 1/48 | (2006.01) |
| A61M 5/14 | (2006.01) |
| B60D 1/52 | (2006.01) |
| B60D 1/00 | (2006.01) |

(52) U.S. Cl.
CPC ............ *A61G 5/10* (2013.01); *A61M 5/1415* (2013.01); *B60D 1/143* (2013.01); *B60D 1/486* (2013.01); *B60D 1/488* (2013.01); *B60D 1/52* (2013.01); *A61G 2200/14* (2013.01); *A61G 2203/80* (2013.01); *A61M 2209/082* (2013.01); *B60D 2001/005* (2013.01)

(58) Field of Classification Search
CPC .......... A61M 5/1415; A61M 2209/082; B60D 1/143; B60D 1/146; B60D 1/486; B60D 1/52; B60D 2001/005; A61G 2200/14; A61G 2203/80
See application file for complete search history.

(56) References Cited

U.S. PATENT DOCUMENTS

| | | | |
|---|---|---|---|
| 4,729,576 A | 3/1988 | Roach | |
| 5,118,127 A | 6/1992 | Partington | |
| 5,292,094 A | 3/1994 | VanKuiken | |
| 5,374,074 A | 12/1994 | Smith | |
| 5,421,548 A | 6/1995 | Bennett et al. | |
| 5,479,953 A * | 1/1996 | Pasulka | A61M 5/1415 135/66 |
| 5,588,166 A | 12/1996 | Burnett | |
| 5,699,988 A | 12/1997 | Boettger et al. | |
| 5,704,577 A | 1/1998 | Gordon | |
| 5,898,961 A * | 5/1999 | Ambach | A61G 7/05 292/108 |
| 5,987,670 A | 11/1999 | Sims et al. | |
| 6,601,860 B2 | 8/2003 | Potter | |
| 7,777,995 B2 | 8/2010 | Malkus et al. | |
| 8,459,602 B2 | 6/2013 | Herskovic | |
| 8,474,839 B2 | 7/2013 | Wenner | |
| 9,511,185 B2 | 12/2016 | Slaker et al. | |
| 10,322,055 B1 * | 6/2019 | Davis | A61H 3/04 |
| 10,555,851 B1 * | 2/2020 | Alahmari | A61G 7/08 |

(Continued)

*Primary Examiner* — Brian L Swenson
(74) *Attorney, Agent, or Firm* — Kelly & Kelley, LLP

(57) ABSTRACT

A chemo mobile cart system for connecting a child transport vehicle to a mobile IV post assembly includes a quick-connect linkage having a platform and a quick-connect arm connectable to the mobile IV post assembly. The platform is releasably connected to the child transport vehicle, and a battery is disposed on the platform together with an inverter electrically connected to the battery. An electrical generator is electrically connected to the battery and disposed on or adjacent to the platform. The electrical generator is mechanically connected to the child transport vehicle and electrically connected to the battery to recharge the battery as the child transport vehicle moves across a support surface.

13 Claims, 6 Drawing Sheets

(56) References Cited

U.S. PATENT DOCUMENTS

| | | | |
|---|---|---|---|
| 2002/0101046 A1* | 8/2002 | Potter | A61G 1/04 280/47.34 |
| 2004/0075228 A1 | 4/2004 | Duffey | |
| 2009/0085317 A1* | 4/2009 | Livengood | A61H 3/04 280/79.3 |
| 2016/0302982 A1 | 10/2016 | Blankenship et al. | |
| 2017/0290633 A1 | 10/2017 | Burke et al. | |
| 2018/0186395 A1* | 7/2018 | Anderson | B62B 5/082 |
| 2019/0054232 A1* | 2/2019 | Cashin | B62K 27/003 |

* cited by examiner

CHEMO MOBILE CART SYSTEM

FIELD OF THE INVENTION

The present invention relates to the transport of medical patients together with a mobile IV post assembly. More specifically, the present invention relates to a mobile cart system for connecting a child transport vehicle to a mobile IV post assembly.

BACKGROUND OF THE INVENTION

Modern hospitals have a need to transport patients from one area to another, for example, for x-rays or some other specialized treatment. Many times these patients require a continuous input of fluid from an intravenous (IV) bag. Typically, these bags contain blood, saline solutions, or some other fluid required by the patient. In order to move the fluid dispensing system with the patient, many mobile IV racks have been developed, but have a number of severe limitations. For example, the patient can move the IV dispenser by themselves if they are able. However, if they are not, for example, if the patient is in a bed or is a child unable to navigate the large, cumbersome and poorly balanced IV dispensers of contemporary design, a nurse or some other hospital personnel must manage the task. This is a serious waste of human resources. Further, by their very nature, these IV dispenser racks are easily toppled since the weight of the fluid bag or bags is at the top, creating a top-heavy design. Current practices for eliminating the inefficiency associated with multiple hospital personnel include attaching IV racks to medical transport vehicles with medical tape, bungee cords, and other temporary measures that create a high risk of accidental toppling.

Some IV racks have been in use which can be separated from their trundles and placed in a holder on a bed. This works well enough for adult patients, but where child patients are involved, the patient transport device may be too small to accommodate this arrangement. For example, many hospitals use small wagons to transport child patients. This mode of transport is both functional and adds an element of fun to a child's experience in the hospital.

During movement about, children will oftentimes be required to travel while connected to an I.V. or other medical device. Being connected to such a medical device also makes a child immobile unless they are being helped. Drip type I.V. bags have not been preferred for use with children since the flow rate can be easily changed by the child and they are not very accurate in flow rate at the lower flow rates of medicine used for children both of which create safety concerns. Typically, children are connected to an infusion pump for intravenous injection to more accurately regulate the injection of medicines or the like than can be accomplished with the drip type I.V. bags and because infusion pumps are relatively tamper resistant. Even though infusion pumps are preferred, they are typically large and heavy, presenting safety concerns should one fall on a child if not properly secured.

Accordingly, there is a need for a chemo mobile cart system for connecting a child transport vehicle to a mobile IV post assembly which easily attaches to both components, and further preferably includes means for providing power to an IV infusion pump. Additionally, it would be advantageous to provide an electrical generator as part of the system which is capable of generating electricity through to movement of the child transport vehicle over a support surface, such as the floor of a hallway of a medical facility. The electrical generator would be electrically connected to a battery to recharge the battery for extended use. The present invention fulfills these needs and provides other related advantages.

SUMMARY OF THE INVENTION

The present invention resides in a chemo mobile cart system for connecting a child transport vehicle to a mobile IV post assembly. The chemo mobile cart system comprises a quick-connect linkage which includes a platform and a quick-connect arm connectable to the mobile IV post assembly. Means are provided for connecting the platform to the child transport vehicle. An IV post clamp is secured to the quick-connect arm opposite the platform, for connecting the quick-connect linkage to the IV post assembly.

A battery and an inverter are disposed on the platform. The inverter is electrically connected to the battery. An electrical generator may also be provided which is electrically connected to the battery and disposed on or adjacent to the platform.

The platform includes a receiver for securely attaching the quick-connect arm to the platform. The means for connecting the platform to the child transport vehicle comprises at least one axle clamp and/or connecting strap for connecting the platform to the child transport vehicle.

The inverter is electrically connectable to an IV machine associated with the IV post assembly.

The electrical generator is mechanically connected to the child transport vehicle and electrically connected to the battery to recharge the battery as the child transport vehicle moves across a support surface. Preferably, the electrical generator is disposed under the platform and secured thereto by at least one generator-securing strap.

Other features and advantages of the present invention will become apparent from the following more detailed description, taking in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
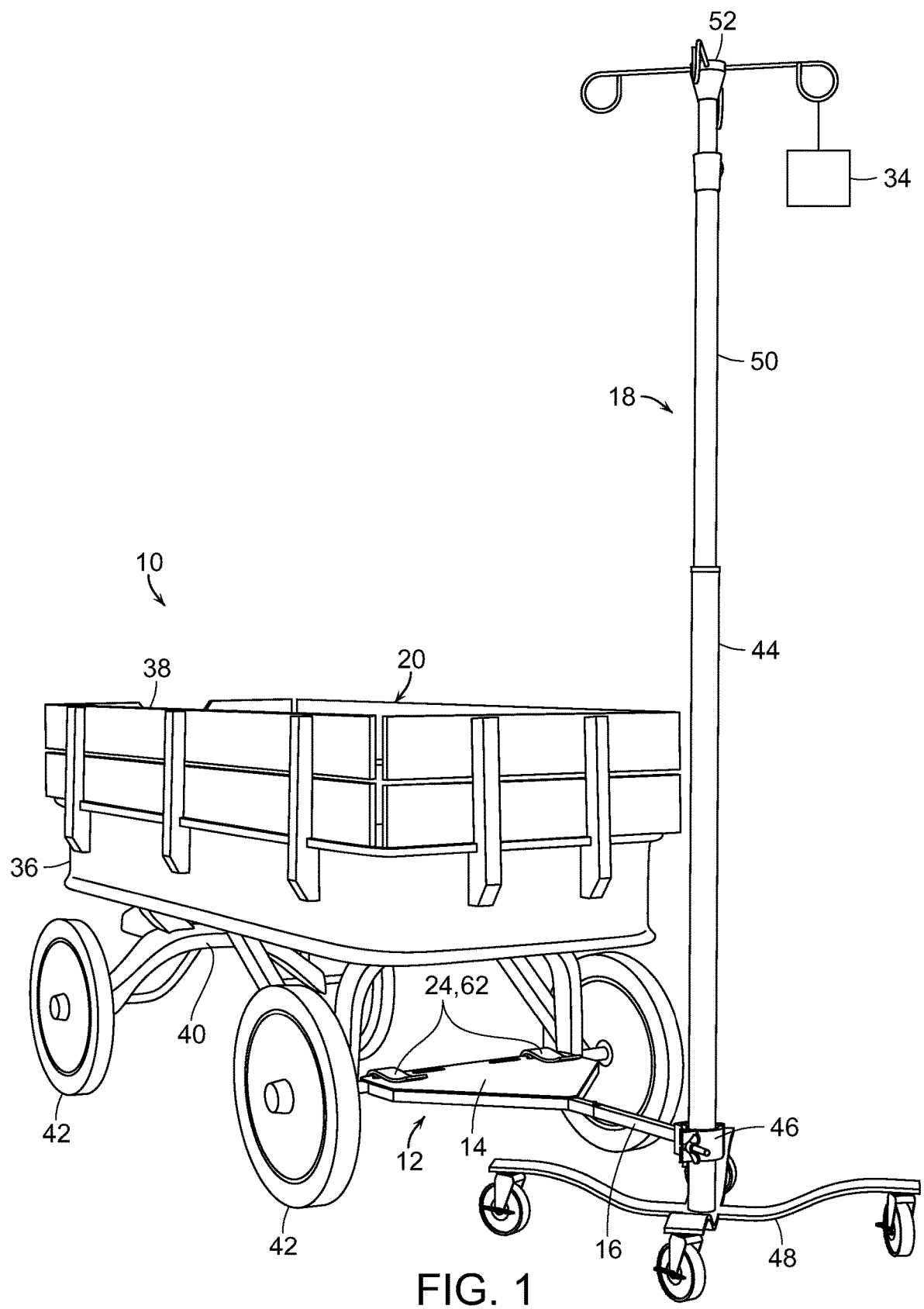
FIG. 1 is a perspective view of a chemo mobile cart system for connecting a child transport vehicle to a mobile IV post assembly, embodying the present invention.

As shown in the drawings for purposes of illustration, the present invention is concerned with a chemo mobile cart system, generally designated in FIG. 1 by the reference number 10. The system 10 comprises, generally, a quick-connect linkage 12 including a platform 14 and a quick-connect arm 16 which is connectable to a mobile IV post assembly 18. The quick-connect linkage 12 also includes means for connecting the platform 14 to a child transport vehicle 20 in the form of a pair of axle clamps 22 and/or connecting straps 24.

Figure 4:
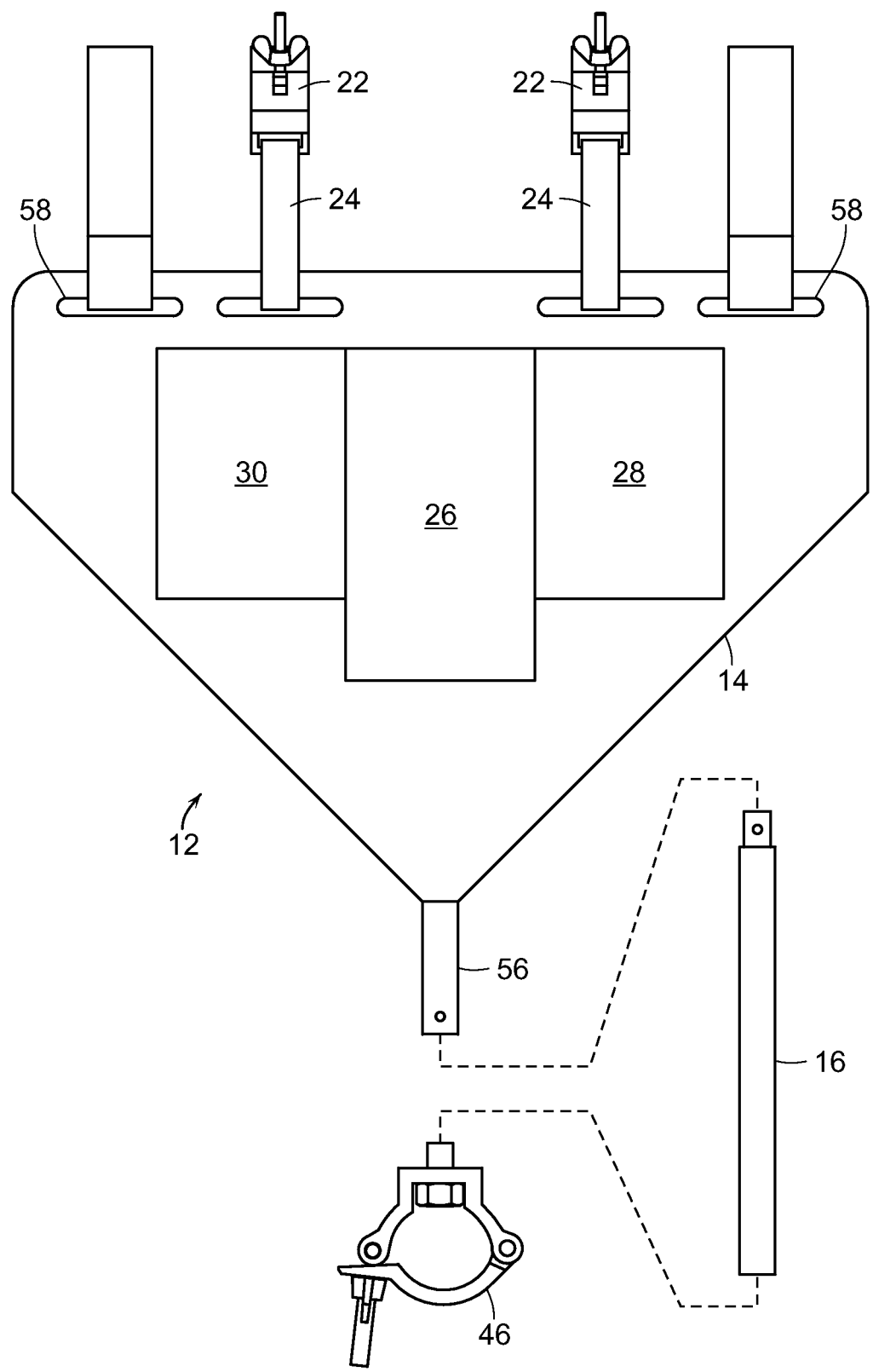
FIG. 4 is an enlarged top plan view of the quick-connect linkage of FIGS. 2 and 3, illustrating placement of a battery, an inverter and a generator on an upper surface of a platform thereof.
Figure 5:
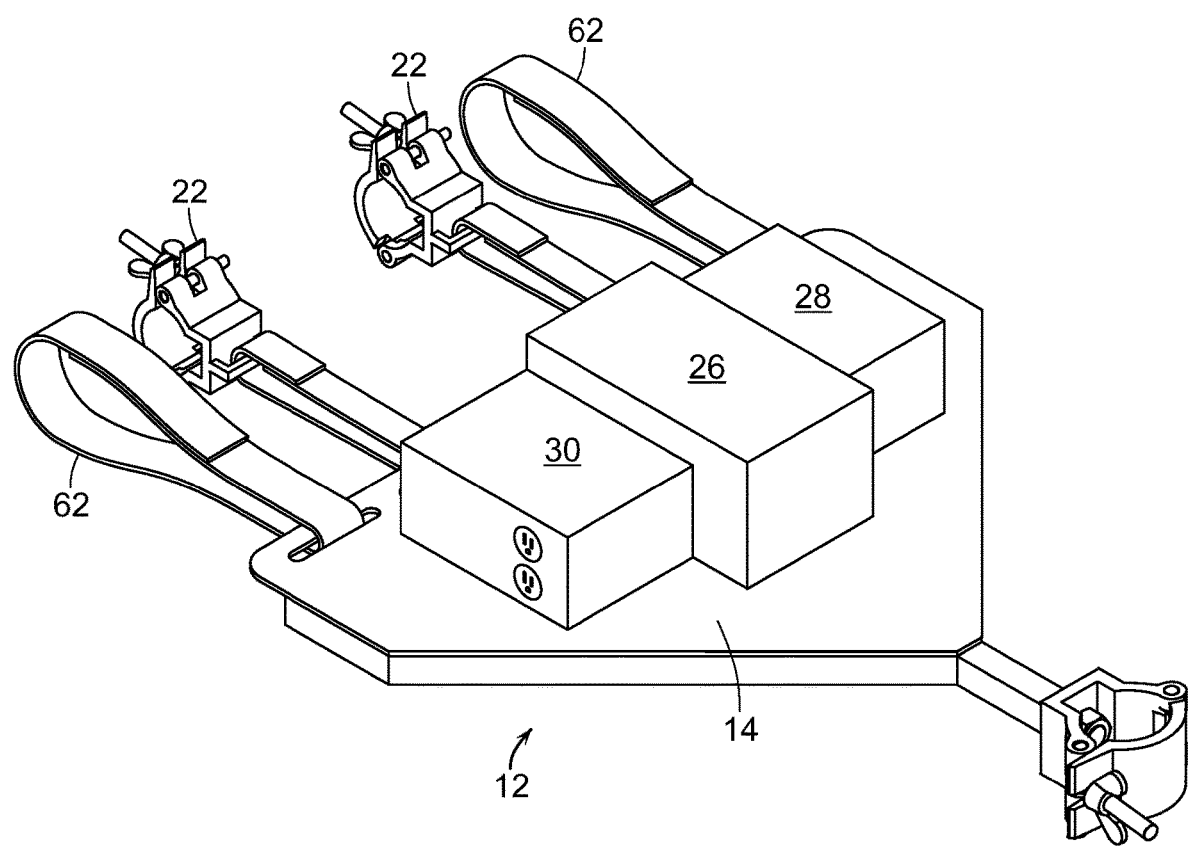
FIG. 5 is a top and side perspective view similar to FIG. 2, illustrating the battery, inverter and generator components of FIG. 4 situated on top of the platform.

As shown in FIGS. 4 and 5 a battery 26, and an inverter 28 and an electrical generator 30 are all disposed on or adjacent to the platform 14. The inverter 28 is electrically connected to the battery 26, and the electrical generator 30 is electrically connected to the battery 26.

Figure 7:
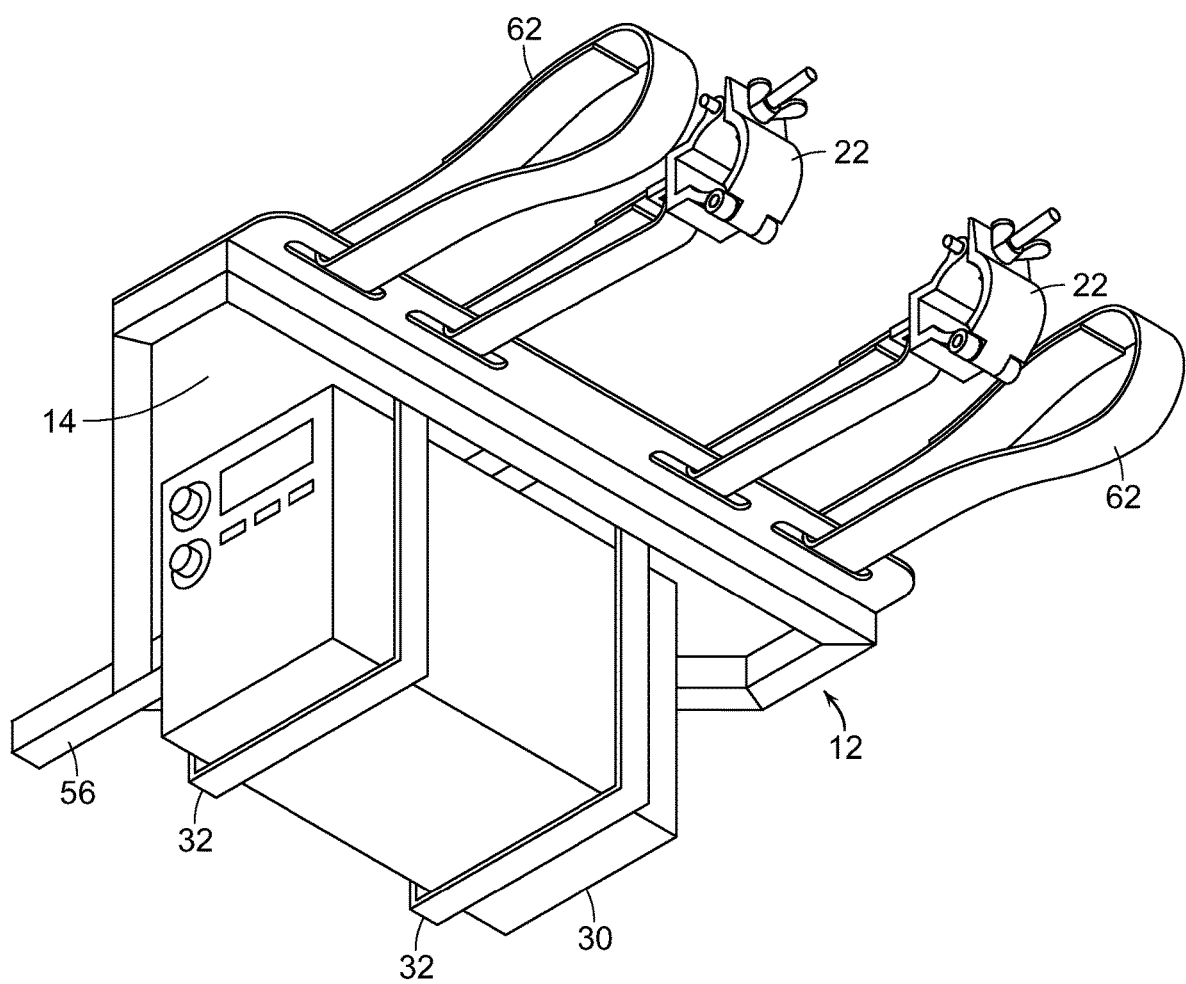
FIG. 7 is a bottom and side perspective view similar to FIG. 3, illustrating an electrical generator mechanically connected to the child transport vehicle and electrically connected to the battery, wherein the electrical generator is disposed under the platform and secured thereto by plurality of generator-securing straps.

As shown in FIG. 7, the electrical generator 30 may be disposed under the platform 14 and secured thereto by a pair of generator-securing straps 32. The inverter 28 is electrically connectable to an infusion pump 34 associated with the mobile IV post assembly 18. The electrical generator 30 is mechanically connected to the child transport vehicle 20 and electrically connected to the battery 26 to recharge the battery as the child transport vehicle 20 moves across a support surface such as a hospital hallway floor.

Referring back to FIG. 1, the child transport vehicle 20 is shown in the form of a wagon that includes a base pan 36 and upwardly extending fencing 38 for safely carrying a child within the wagon. The wagon 20 includes an undercarriage 40 which connects the base pan 36 to four wheels 42.

The child transport vehicle or wagon 20 is connected to an outer IV post 44 of the mobile IV post assembly 18 by means of a quick connect IV post clamp 46. The mobile IV post assembly 18 comprises a wheel assembly 48 which supports and is connected to a lower end of the outer IV post 44. An inner IV post 50 adjustably extends upwardly from the outer IV post 44 to a hanger assembly 52 whereon drip-type IV bags or, as shown, an infusion pump 34 may be positioned.

Figure 2:
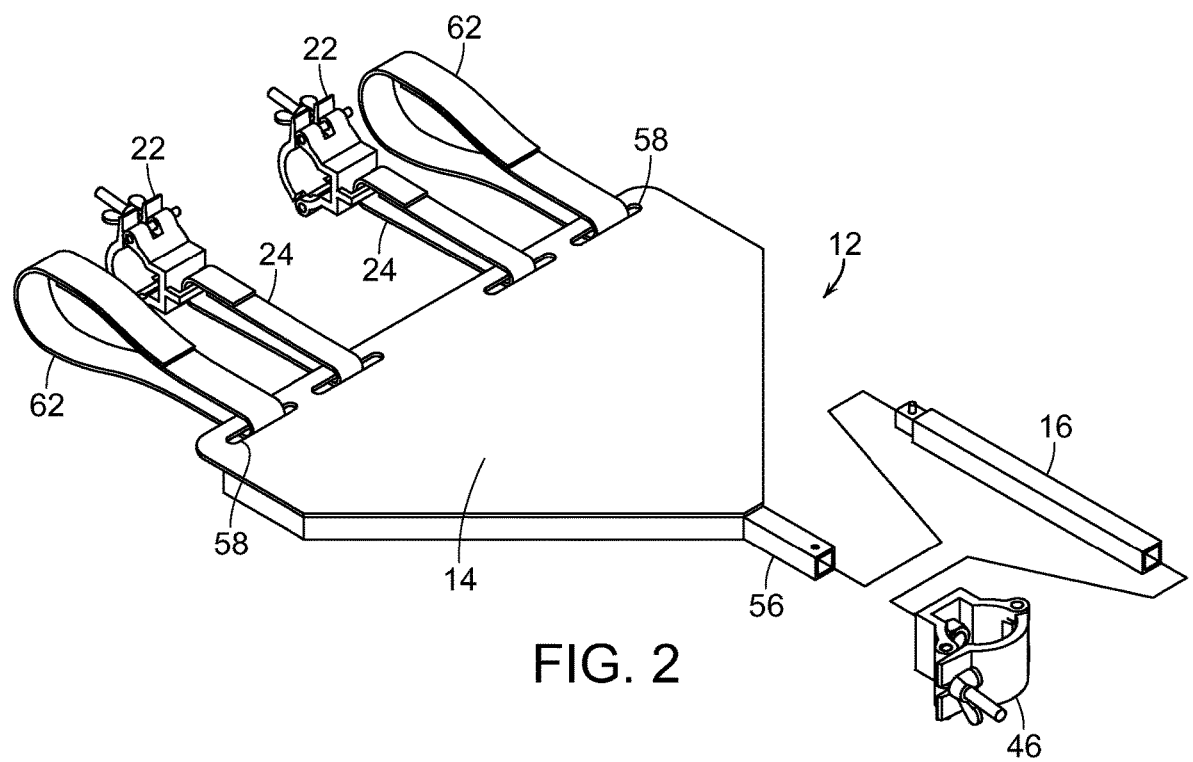
FIG. 2 is an enlarged top and side perspective view of the quick-connect linkage shown in FIG. 1, for connecting the child transport vehicle to the mobile IV post assembly.
Figure 3:
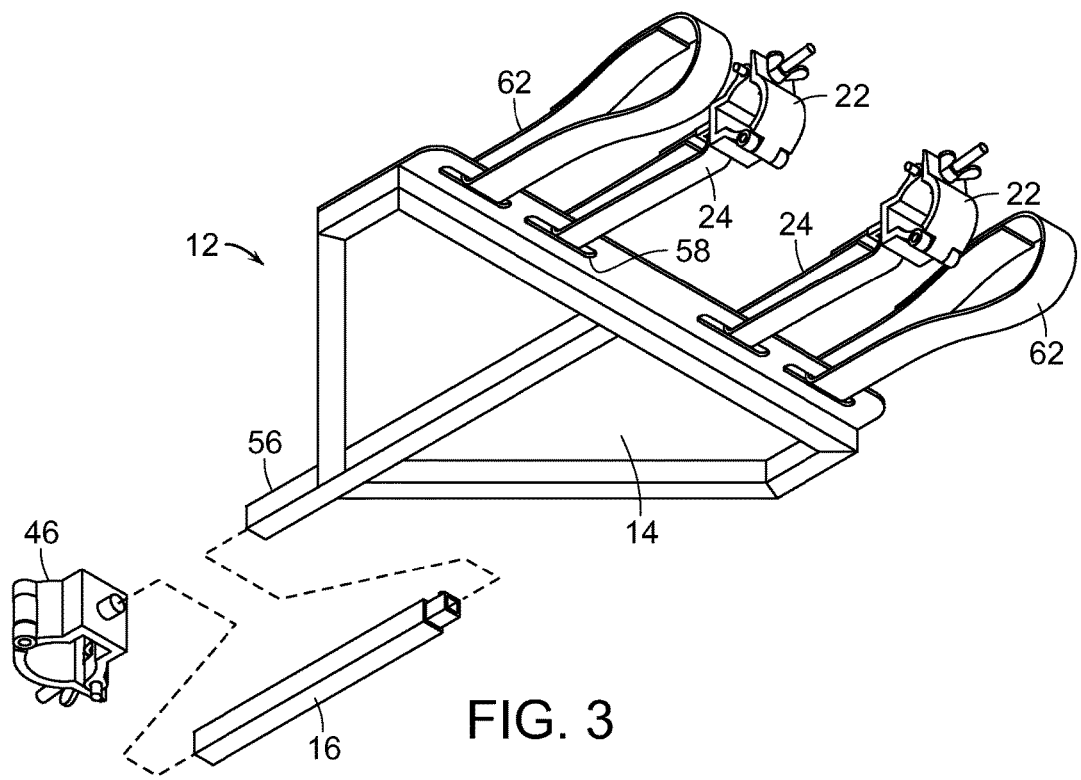
FIG. 3 is a bottom and side perspective view of the quick-connect linkage of FIG. 2.

FIGS. 2 and 3 show the top and bottom of the quick connect linkage 12 illustrated in FIG. 1. As shown, the quick connect linkage 12 includes a relatively planar platform 14 and a forwardly extending quick connect arm 16 disposed within a quick connect arm receiver 56. Opposite the quick connect arm receiver, the quick connect arm 16 includes a quick connect IV post clamp 46 which may be positioned and tightened to lock onto a lower end of the outer IV post 44.

The rear end of the platform 14 includes four slots 58 through which various straps are past. The connecting straps 24 passing through the inner slots are connected to axle clamps 22 which may be manipulated to grasp and be tightened to an axle or another portion of the undercarriage 40 of the wagon 20. The outer straps 62 may be looped about the axle or another part of the undercarriage 14 as a safety connection or they may provide simply an alternative form of connecting the platform 14 to the undercarriage 40. Preferably all of the straps 24, 62 are provided with a hook and loop fastener attachments to permit the straps to be adjustably fitted and secured to the undercarriage 40 of the wagon 20.

FIGS. 4 and 5 illustrate how the battery 26, the inverter 28 and the electrical generator 30 may all be disposed on an upper surface of the platform 14 of the quick connect linkage 12.

Figure 6:
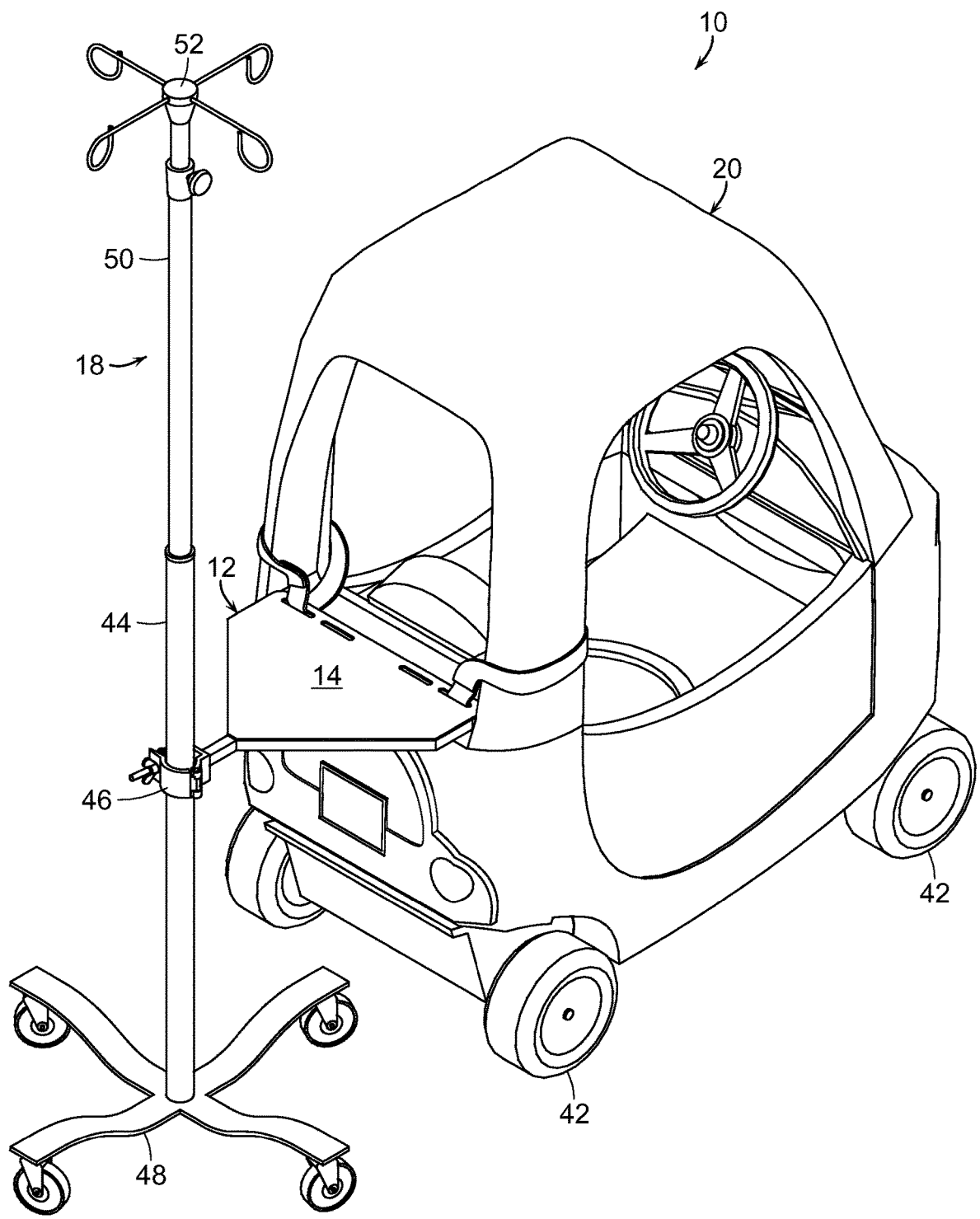
FIG. 6 is a perspective view similar to FIG. 1, illustrating the chemo mobile cart system of the present invention attached to an alternative child transport vehicle, wherein the mobile IV post is pulled behind the child transport vehicle.

FIG. 6 illustrates how the quick connect linkage 12 may be utilized in a configuration where the mobile IV post assembly 18 is to be pulled behind the child transport vehicle 20, rather than the situation shown in FIG. 1 where the child transport vehicle or wagon 20 is configured to be pulled behind the mobile IV post assembly 18.

FIG. 7 shows that the electrical generator 30 may be disposed under the platform 14 and secured thereto by a pair of generator-securing straps 32, rather than being disposed on the upper surface of the platform as shown in FIGS. 4 and 5. Regardless of the actual position of the electrical generator, its purpose is to be mechanically connected to the child transport vehicle 20 to harvest mechanical energy generated by moving the child transport vehicle 20 over a support surface such as a hospital hallway or floor, and convert the mechanical energy into electrical energy that can then be directed to recharge the battery 26. The inverter 28 is provided to convert the DC current output from the battery 26 to required AC current for the infusion pump 28 to allow continuous operation of the infusion pump as the chemo mobile cart system 10 is utilized to transport a child.

Although several embodiments of the invention have been described in detail for purposes of illustration, various modifications may be made without departing from the spirit and scope of the invention. Accordingly, the invention is not to be limited, except as by the appended claims.

What is claimed is:

1. A chemo mobile cart system for connecting a child transport vehicle to a mobile IV post assembly, comprising:
   a quick-connect linkage including a platform and a quick-connect arm connectable to the mobile IV post assembly;
   means for connecting the platform to the child transport vehicle;
   a battery disposed on the platform;
   an inverter electrically connected to the battery and disposed on the platform; and
   an electrical generator electrically connected to the battery and disposed on or adjacent to the platform.

2. The system of claim 1, wherein the platform includes a receiver for securely attaching the quick-connect arm to the platform.

3. The system of claim 1, wherein the means for connecting the platform to the child transport vehicle comprises at least one axle clamp for connecting the platform to the child transport vehicle.

4. The system of claim 1, wherein the means for connecting the platform to the child transport vehicle comprises at least one connecting strap for connecting the platform to the child transport vehicle.

5. The system of claim 1, wherein the inverter is electrically connectable to an IV machine associated with the IV post assembly.

6. The system of claim 1, wherein the electrical generator is disposed under the platform and secured thereto by at least one generator-securing strap.

7. The system of claim 1, wherein the electrical generator is mechanically connected to the child transport vehicle and electrically connected to the battery to recharge the battery as the child transport vehicle moves across a support surface.

8. A chemo mobile cart system for connecting a child transport vehicle to a mobile IV post assembly, comprising:

a quick-connect linkage including a platform and a quick-connect arm connectable to the mobile IV post assembly;
means for connecting the platform to the child transport vehicle;
a battery disposed on the platform;
an inverter electrically connected to the battery and disposed on the platform;
an IV post clamp secured to the quick-connect arm opposite the platform, for connecting the quick-connect linkage to the IV post assembly; and
an electrical generator electrically connected to the battery and disposed on or adjacent to the platform.

9. The system of claim 8, wherein the electrical generator is mechanically connected to the child transport vehicle and electrically connected to the battery to recharge the battery as the child transport vehicle moves across a support surface.

10. The system of claim 9, wherein the electrical generator is disposed under the platform and secured thereto by at least one generator-securing strap.

11. The system of claim 8, wherein the inverter is electrically connectable to an IV machine associated with the IV post assembly.

12. The system of claim 8, wherein the platform includes a receiver for securely attaching the quick-connect arm to the platform.

13. The system of claim 8, wherein the means for connecting the platform to the child transport vehicle comprises at least one axle clamp and/or connecting strap for connecting the platform to the child transport vehicle.

* * * * *